United States Patent [19]

Van de Sande et al.

[11] Patent Number: 4,458,011

[45] Date of Patent: Jul. 3, 1984

[54] BALLASTED COMPOUNDS AND PHOTOGRAPHIC ELEMENTS CONTAINING SUCH COMPOUNDS

[75] Inventors: Christian C. Van de Sande, Belsele; Jan J. Vandewalle; Marcel J. Monbaliu, both of Mortsel; Raphaël K. Van Poucke; Berchem; all of Belgium

[73] Assignee: AGFA-Gevaert, N.V., Mortsel, Belgium

[21] Appl. No.: 437,861

[22] Filed: Oct. 29, 1982

[30] Foreign Application Priority Data

Nov. 12, 1981 [GB] United Kingdom ............... 8134157

[51] Int. Cl.$^3$ ............................................. G03C 7/26
[52] U.S. Cl. ................................. 430/543; 430/214; 430/222; 430/512; 430/551; 430/552; 430/553; 430/554; 430/555; 430/556; 430/557; 430/558; 430/559
[58] Field of Search ............... 430/552, 553, 554, 555, 430/556, 557, 558, 559, 512, 214, 551, 543

[56] References Cited

U.S. PATENT DOCUMENTS 3,622,337 11/1971 Altaville et al. .................. 430/552
4,205,987 6/1980 Erikson et al. .................... 430/223

FOREIGN PATENT DOCUMENTS 60696 3/1968 German Democratic Rep. ..

OTHER PUBLICATIONS

Chemical Abstracts, vol. 70, Item 24614z, 1969.

Primary Examiner—J. Travis Brown
Attorney, Agent, or Firm—A. W. Breiner

[57] ABSTRACT

The present invention relates to compounds of the type comprising a ballasting group which renders said compounds substantially fast to diffusion in hydrophilic colloid media and at least one photographically useful group which is chemically linked to said ballasting group, and to photographic elements containing at least one compound of the type referred to.

The ballasting groups in the compounds according to the present invention are derived from mono- or di-esters or -ethers of glycerol. The linkage between ballasting group and photographically useful group can be realized via acid chlorides which are derived from the above-said glycerol derivatives.

5 Claims, No Drawings

BALLASTED COMPOUNDS AND PHOTOGRAPHIC ELEMENTS CONTAINING SUCH COMPOUNDS

The present invention relates to compounds of the type comprising a ballasting group which renders said compounds substantially fast to diffusion in hydrophilic colloid media and at least one photographically useful group which is chemically linked to said ballasting group, and to photographic elements containing at least one compound of the type referred to.

In photography in general and in colour photography and diffusion transfer processes in particular it is necessary that at least some of the photographically useful ingredients or compounds of a photographic material remain steadily fixed in the hydrophilic layer or layers in which they have originally been incorporated.

In order to obtain excellent colour images for instance, colour separation has to be quite perfect indeed and therefore it is essential that colour couplers and mask-forming compounds, when incorporated in photographic light-sensitive emulsions, remain perfectly immobile in the hydrophilic colloid layer in which they were originally incorporated and that they do not start wandering or diffusing through the photographic material.

The problem of inter-layer diffusion of photographically useful compounds is well-known in the art and has already been extensively described in quite a lot of patents and other publications. From the latter publications one can learn that diffusion of photographically useful compounds through hydrophilic colloid layers can advantageously be prevented by providing said photographically useful compounds with one or more ballasting groups. Such groups generally consist of or comprise long straight or branched aliphatic hydrocarbon chains (e.g. of from 5 to 20 or more C-atoms) and their incorporation into photographically useful compounds involves no particular synthetical problems. Examples of ballasting groups known to be relatively useful in photography are given e.g. in DE-OS No. 2,418,959 and GB Pat. No. 1,336,171.

The said ballast groups impart to the molecules a hydrophobic character. The said ballasted molecules are incorporated into hydrophilic colloid compositions either as dispersions or in the form of solutions. In the latter case the ballasted molecules should be provided with solubilizing groups e.g. carboxyl and/or sulpho groups.

More frequently, however, the ballasted compounds are incorporated into the hydrophilic colloid media according to well-known dispersion techniques. For this purpose the compounds can be dissolved in a low-boiling or high-boiling water-immiscible solvent or mixture thereof whereupon the solution is dispersed into water or into an aqueous solution of a hydrophilic colloid with the aid of one or more dispersing agents. After removal of the low-boiling solvent the dispersion is admixed with the coating composition of the hydrophilic colloid layer of a photographic material.

Photographically useful compounds, which in the manufacture of photographic silver halide material have to be incorporated into one or more hydrophilic colloid layers of said material as ballasted compounds, include amongst others colour couplers, competing couplers, mask-forming compounds, UV-absorbers, stabilizers, anti-oxidants and dyes.

By colour coupler is meant any compound which in silver halide photography couples with an oxidized aromatic primary amino colour developing agent to form a dye image.

Competing couplers are compounds which are used in conjunction with colour couplers in silver halide colour photography and which couple with the oxidized aromatic primary amino colour developing agent to form colourless coupling products, e.g. as described in GB Pat. No. 861,138.

By mask-forming compounds are meant compounds which oxidatively couple with colour couplers in an oxidizing bleaching bath in order to form coloured mask images as described, e.g., in GB Pat. Nos. 880,862 and 975,932.

As is well-known in all types of diffusion transfer processes certain compounds such as e.g. dyes, colour couplers, redox-dye releasing compounds, electron-donor compounds, scavenger compounds for oxidized developing agents, etc. have to be retained in their original hydrophilic colloid layer, at least for a controllable period of time.

Several dye-diffusion transfer systems are described, e.g., in GB Pat. Nos. 1,243,048 and 1,405,662; U.S. Pat. Nos. 3,227,550, 3,628,952, 4,030,920, 4,139,379, 4,139,389; published U.S. Ser. No. B 351,673; DE-OS No. 2,645,656; Eur. Pat. No. 0004399; Eur. Pat. Appl. Nos. 79 200 117.4 and 81 200 303.6 and GB Pat. Appl. No. 80 31,433.

Compounds of the type referred to hereinbefore and provided with the conventional well-known ballasting groups present some drawbacks in that they often crystallize from their dispersions and in that the dispersions are too coarse.

It is an object of the present invention to provide novel ballasted compounds which, when dispersed into hydrophilic colloid layers of photographic materials do not present the above drawbacks.

The present invention provides ballasted compounds comprising one or more photographically useful groups and a ballasting group that is structurally derived from glycerol wherein one or two —OH group(s) is/are converted to —OR group(s) and the remaining —OH group(s) is/are converted to —X—L— molecular parts linking the said ballasting group to the said photographically useful group or groups and wherein:

R is an organic group, with the proviso that, when two of said —OR groups are present, the said —R groups together contain not less than 5 hydrocarbon C-atoms;

X is —O—, —S— or —NY—, where Y is H or a $C_1$–$C_5$ alkyl group, and

L is a chemical bond or a group, linking X to the said photographically useful group or groups.

The ballasting groups defined in the present invention are derived from mono- or di-esters of from mono- or di-ethers of glycerol and the linkage of a ballasting group to a photographically useful group can be realized via an acid chloride intermediate of the glycerol derivative.

In general the ballasting molecular moieties of the compounds of the invention are mono- or di-esters of glycerol and the said compounds may contain one or two photographically useful groups. Such photographically useful groups may be any group used in a photographic process, for example colour couplers, competing couplers, mask-forming compounds, UV-absorbers, stabilizers, anti-oxidants, dyes and compounds particularly for use in diffusion transfer processes as defined hereinbefore.

A ballasting group as defined in the present invention comprises a glycerol-based nucleus that can be considered as a suitable link, having already some ballasting properties of its own, between one or two photographically useful groups as defined hereinbefore and one or two bulking $C_1-C_5$ alkyl groups.

When one photographically useful group is attached to the glycerol-derived ballasting group the said alkyl groups must together contain a minimum number of hydrocarbon C-atoms as hereinbefore set forth.

When two photographically useful groups are present, however, each of said photographically useful groups is acting as a ballasting group with respect to the other, so that no such minimum number of hydrocarbon C-atoms is imposed in respect of the bulking $C_1-C_5$ alkyl group.

A ballasting group as defined hereinbefore preferably corresponds to one of the following general formulae:

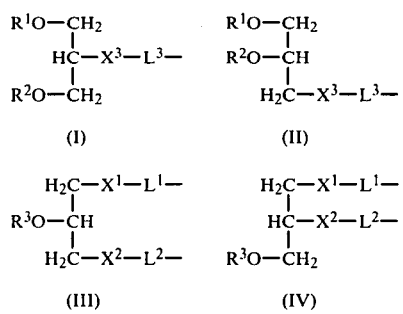

wherein:
each of $X^1$, $X^2$, $X^3$ (the same or different) represents —O—, —S— or —NY—, wherein Y stands for hydrogen or a $C_1-C_5$ alkyl group;
each of $L^1$, $L^2$, $L^3$ (the same or different) stands for a chemical bond or a bivalent mono- or polyatomic group, e.g. selected from —CO—, —SO$_2$—, —CO—O—, —CO—NY'—, —CO—CO—NY'—, —SO$_2$—NY'—, wherein Y' is hydrogen or a $C_1-C_5$ alkyl group, or from alkylene, arylene, substituted alkylene or substituted arylene, and
each of $R^1$, $R^2$, $R^3$ (the same or different) stands for alkyl, aryl, acyl and/or substituted alkyl, aryl, acyl (e.g. alkylcarbonyl, alkylsulphonyl, alkylaminocarbonyl, alkoxycarbonyl, dialkylaminocarbonyl ...) with the proviso that $R^1+R^2$ comprise together at least 5 hydrocarbon C atoms.

The above-said photographically useful compounds are e.g. colour couplers, competing couplers, mask-forming compounds, UV-absorbers, stabilizers, dyes, dye-providing compounds, electron-donor compounds, scavenger compounds and anti-oxidants.

We have found that compounds bearing a ballasting group corresponding to one of the general formulae given hereinbefore, present some particularly interesting advantages over similar compounds consisting of the same photographically useful group but having a ballasting moiety of a different type. For instance, the ballasting moieties of compounds according to the present invention have a favourable influence upon the micro-structure of a dispersion of such ballasted compounds. Further, they can favourably influence the conformation of colour couplers and their coupling kinetics. Moreover, the conformation of a quinone-imine or azomethine dye can be modified by introducing a ballasting moiety according to the invention into the coupler from which the dye has to be formed.

Photographically useful compounds ballasted according to the present invention can systematically and easily be dispersed in water or in aqueous hydrophilic colloids independent of the intrinsic structure of the compound and this advantageously permits the preparation of highly concentrated aqueous dispersions of said compounds according to the methods referred to hereinbefore and described e.g. in U.S. Pat. No. 3,658,546; DE-AS No. 1,127,714; U.S. Pat. No. 2,322,027 and GB Pat. No. 1,297,947.

Examples of compounds according to the present invention are listed in the following tables.

TABLE I

Magenta-forming 2-pyrazolin-5-one colour couplers.

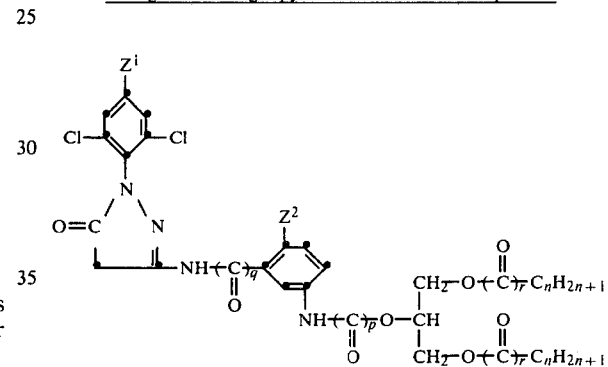

| Compound | $Z^1$ | $Z^2$ | q | p | r | n | Melting point (°C.) |
|---|---|---|---|---|---|---|---|
| 1 | —Cl | —H | 1 | 1 | 0 | 6 | 156 |
| 2 | —Cl | —H | 1 | 1 | 0 | 8 | 70-130 |
| 3 | —Cl | —H | 1 | 2 | 0 | 6 | 128 |
| 4 | —Cl | —H | 1 | 2 | 0 | 8 | 155 |
| 5 | —Cl | —H | 1 | 2 | 0 | 10 | 110 |
| 6 | —Cl | —H | 1 | 2 | 1 | 9 | 100 |
| 7 | —Cl | —Cl | 0 | 1 | 0 | 6 | 108-110 |
| 8 | —Cl | —Cl | 0 | 1 | 0 | 8 | 65-75 |
| 9 | —Cl | —Cl | 0 | 2 | 0 | 6 | 94 |
| 10 | —Cl | —Cl | 0 | 2 | 0 | 8 | 65-84 |
| 11 | —OCH$_3$ | —H | 1 | 1 | 0 | 6 | 130 |
| 12 | —OCH$_3$ | —H | 1 | 1 | 0 | 8 | 130-138 |
| 13 | —OCH$_3$ | —H | 1 | 2 | 0 | 6 | 66-100 |
| 14 | —OCH$_3$ | —H | 1 | 2 | 0 | 8 | 100 |
| 15 | —OCH$_3$ | —H | 1 | 2 | 0 | 10 | 50-80 |
| 16 | —OCH$_3$ | —H | 1 | 2 | 1 | 9 | oil |
| 17 | —SO$_2$N(CH$_3$)$_2$ | —Cl | 0 | 1 | 0 | 8 | 80 |
| 18 | —SO$_2$CH$_3$ | —Cl | 0 | 1 | 0 | 6 | 160 |
| 19 | —SO$_2$CH$_3$ | —Cl | 0 | 1 | 0 | 8 | 155 |
| 20 | —SO$_2$CH$_3$ | —Cl | 0 | 2 | 0 | 6 | 84-110 |
| 21 | —SO$_2$CH$_3$ | —Cl | 0 | 2 | 0 | 8 | 75-85 |

TABLE II
Magenta-forming 2-pyrazolin-5-one colour couplers.

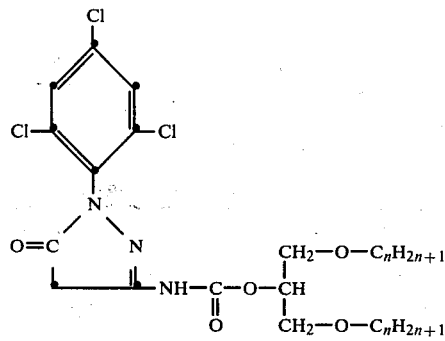

| Compound | n | Melting point (°C.) |
|---|---|---|
| 22 | 6 | 75 |
| 23 | 8 | 76 |

TABLE III
Magenta-forming 2-pyrazolin-5-one colour couplers.

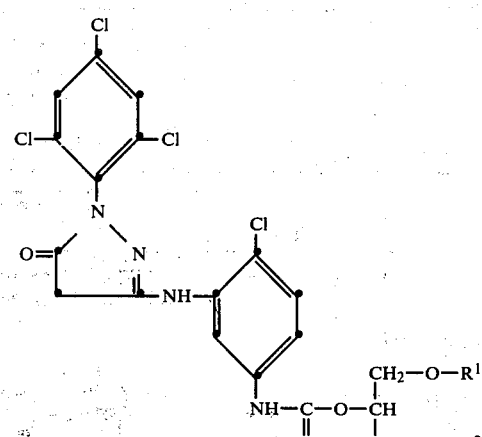

| Compound | R¹ | R² | Melting point (°C.) |
|---|---|---|---|
| 24 | —C$_6$H$_5$ | -nC$_8$H$_{17}$ | 74–80 |
| 25 | —C$_4$H$_9$ | -2-ethylhexyl | 68–72 |

TABLE IV
Yellow-forming benzoylacetanilide colour couplers.

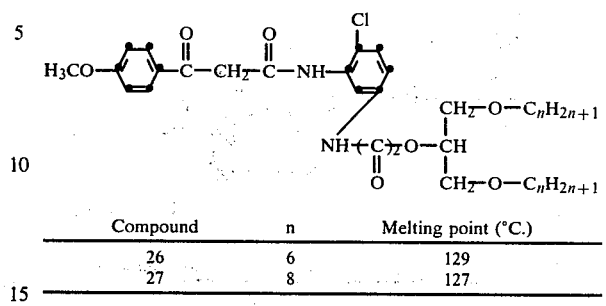

| Compound | n | Melting point (°C.) |
|---|---|---|
| 26 | 6 | 129 |
| 27 | 8 | 127 |

TABLE V
Yellow-forming benzoylacetanilide colour couplers.

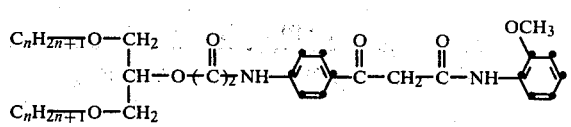

| Compound | n | Melting point (°C.) |
|---|---|---|
| 28 | 8 | 112 |
| 29 | 6 | 110 |

TABLE VI
Yellow-forming benzoylacetanilide colour couplers.

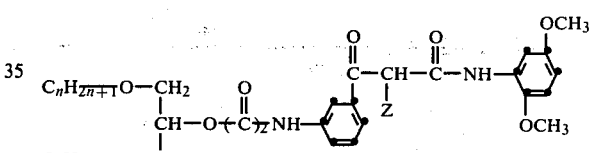

| Compound | Z | n | Melting point (°C.) |
|---|---|---|---|
| 30 | 7-theophyllinyl | 6 | resin |
| 31 | " | 8 | resin |

TABLE VII
Yellow-forming benzoylacetanilide colour couplers.

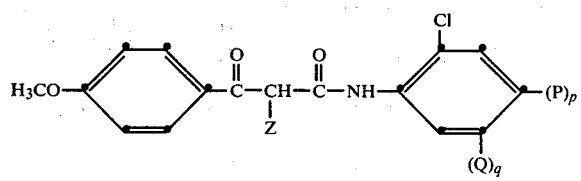

| Compound | Z | p | q | P | Q |
|---|---|---|---|---|---|
| 32 | 7-theophyllinyl | 0 | 1 | — | —CO—O—CH(CH$_2$OC$_8$H$_{17}$)$_2$ |
| 33 | 3,5-dimethyl-pyrazolyl | 0 | 1 | — | —CO—O—CH(CH$_2$OC$_8$H$_{17}$)$_2$ |
| 33bis | H | 1 | 0 | —O—CH(CH$_2$OC$_6$H$_{13}$)$_2$ | — |

TABLE VIII

Yellow-forming pivaloylacetanilide colour couplers.

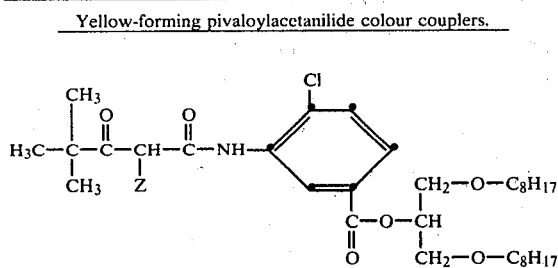

| Compound | Z | p | n | Melting point (°C.) |
|---|---|---|---|---|
| 34 | —H | 2 | 8 | oil |
| 35 | 7-theophyllinyl | 1 | 6 | 131 |
| 36 | " | 1 | 8 | 118 |

TABLE IX

Yellow-forming pivaloylacetanilide colour couplers.

| Compound | Z | Melting point (°C.) |
|---|---|---|
| 37 | 7-theophyllinyl | oil |
| 38 | —OCCH$_3$ (O) | oil |

TABLE X

Cyan-forming phenol colour couplers.

| Compound | Z | p | q | n | Melting point (°C.) |
|---|---|---|---|---|---|
| 39 | —OCH$_3$ | 2 | 0 | 6 | 84 |
| 40 | —OCH$_3$ | 2 | 0 | 8 | <50 |
| 41 | —OCH$_3$ | 2 | 1 | 9 | 89–90 |
| 42 | —Cl | 2 | 0 | 8 | 107–110 |
| 43 | —Cl | 2 | 0 | 6 | 113 |
| 44 | —H | 2 | 0 | 6 | <50 |
| 45 | —H | 2 | 0 | 8 | 85 |
| 46 | —H | 1 | 0 | 6 | 89 |
| 47 | —Cl | 1 | 0 | 6 | 91 |
| 48 | —Cl | 1 | 0 | 8 | 80–82 |
| 49 | —OCH$_3$ | 1 | 0 | 6 | 98 |
| 50 | —OCH$_3$ | 1 | 0 | 8 | 81 |

TABLE XI

Cyan-forming phenol colour couplers.

| Compound | Z | p | n | Melting point (°C.) |
|---|---|---|---|---|
| 51 | —OCH$_3$ | 2 | 8 | 65–66 |
| 52 | —OCH$_3$ | 1 | 6 | 78–79 |
| 53 | —OCH$_3$ | 1 | 8 | 70 |
| 54 | —Cl | 1 | 6 | 93–94 |
| 55 | —Cl | 2 | 6 | 125 |
| 56 | —Cl | 2 | 8 | 121 |

TABLE XII

Cyan-forming phenol colour couplers.

| Compound | Melting point |
|---|---|
| 57 | resin |

TABLE XIII

Cyan-forming phenol colour couplers.

| Compound | p | n | Melting point (°C.) |
|---|---|---|---|
| 58 | 2 | 6 | 99 |
| 59 | 1 | 6 | 107 |
| 60 | 1 | 8 | 97 |

TABLE XIV

Cyan-forming phenol colour couplers.

| Compound | Z | p | n | Melting point (°C.) |
|---|---|---|---|---|
| 61 | —OCH$_3$ | 1 | 6 | 112 |
| 62 | —OCH$_3$ | 1 | 8 | 93 |
| 63 | —OCH$_3$ | 2 | 8 | 113–114 |
| 64 | —H | 1 | 8 | 94–95 |
| 65 | —Cl | 1 | 8 | 104 |

TABLE XV

| Compound | Cyan-forming phenol colour coupler. | Melting point (°C.) |
|---|---|---|
| 66 | 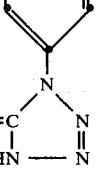 | 156 |

TABLE XVI

| Compound | Type | Formula | Melting point (°C.) |
|---|---|---|---|
| 67 | stabilizer | 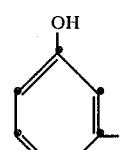 | 50 |
| 68 | black coupler of the type described in DE-OS 2,644,194 |  | viscous oil |
| 69 | UV-absorber |  | <50 |
| 70 | scavenger compound for use in diffusion transfer processes of the type described in U.S. Pat. No. 4,205,987 | | <50 |
| 71 | dye providing compound for use in diffusion transfer processes of the type described in Eur. Pat. Appl. 79 200 117.4 | 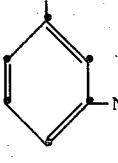 | resin |

The ballasted compounds according to the present invention can be prepared as is illustrated hereinafter.
Key compounds used in the preparation of compounds according to the present invention are mono- or di-esters or -ethers derived from glycerol. They can be prepared as follows.

1,3-Diesters of glycerol can be prepared from 1,3-dihydroxyacetone according to a procedure described by P. H. Bentley and W. Mc.Crae, J.Org.Chem. 35, 2082 (1970):

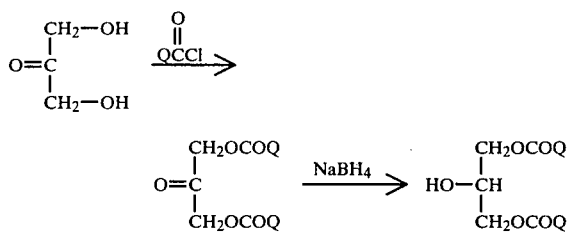

wherein Q is alkyl or aryl including substituted alkyl or aryl.

Symmetrical 1,3-dialkyl ethers of glycerol can be prepared by treating epichlorohydrin with two equivalents of sodium alkoxide:

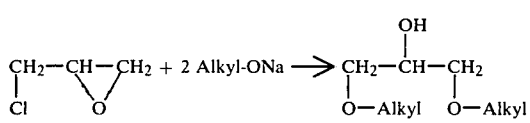

e.g. as described by C. Piantadosi, I. H. Hall, S. D. Wyrick and K. S. Ishaq, J.Med.Chem. 19 (2), 222 (1976). The corresponding symmetrical 1,3-diaryl ethers are similarly prepared using sodium phenolates as nucleophilic reagents (see e.g. S. D. Wyrick and C. Piantadosi, J.Med.Chem. 21 (4), 386 (1978). The preparation of 1,3-di-n-hexyloxy-2-propanol is given hereinafter as an example of the synthesis of a symmetrical 1,3-dialkyl ether.

230 g (10 mol) of sodium grains were added to 2540 g of n-hexanol under vigorous stirring. When all the sodium was dissolved, 392 ml (5 mol) of epichlorohydrin was added at a temperature of about 100° C. The temperature rose and the mixture started refluxing. After subsiding, the mixture was stirred for 3 h while the reaction temperature was maintained at about 130° C. After cooling, the mixture was poored into 3000 ml of toluene and 2000 ml of water. The phases were separated and the organic layer was washed with water and was concentrated in a rotary evaporator. Subsequent fractionation yielded 765 g of the analytically pure product (boiling point: 126° C./7 Pa).

The synthesis of unsymmetrical alkyl and aryl diethers of glycerol, on the other hand, requires the use of glycidyl ethers (of which several are commercially available) as starting materials. These glycidyl ethers can be prepared as described by J. Novak, Coll.Czech.-Chem.Commun. 32, 3794 (1967); U.S. Pat. No. 3,102,912; A. F. Isbell and D. W. Hood, J. Chem.Eng..Data 7, Pt.2, 575 (1962); W. J. Rzeszotarski, R. E. Gibson, W. C. Eckelman and R. C. Reba, J.Med.Chem. 22, 735 (1979). Reaction of these glycidyl ethers with alcohols or phenols yields unsymmetrical 1,3-diethers of glycerol as described in several of the above-mentioned publications. The preparation of 1-phenoxy-3-n-octyloxy-2-propanol is given hereinafter as an example of the synthesis of an unsymmetrical diether of glycerol.

143 g (1.1 mol) of n-octanol was dissolved in 500 ml of dry xylene and 185 ml of 30% sodium methylate in methanol was added. A Dufton column was mounted and the mixture was heated to reflux. Slow destillation was continued until 400 ml of destillate was obtained (containing 165 ml of methanol). Then 150 g (1 mol) of phenylglycidyl ether was quickly added with vigorous stirring whereupon gentle refluxing was maintained for 4 h. After cooling to room-temperature the reaction mixture was poured into water. Extraction with ether, drying over potassium carbonate, filtration and concentration yielded 282 g of crude product which upon fractional destillation yielded 58.5 g of the analytically pure compound (boiling range: 160°-164° C./20 Pa).

The 1,2-diesters or 1,2-dialkyl ethers derived from glycerol can be prepared starting from 1-O-benzyl-glycerol (B. T. Golding and P. V. Ioannou, Synthesis 1977, 423-424) according to the following general reaction schemes:

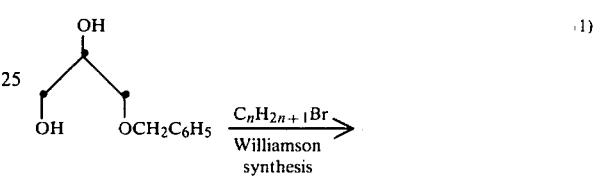

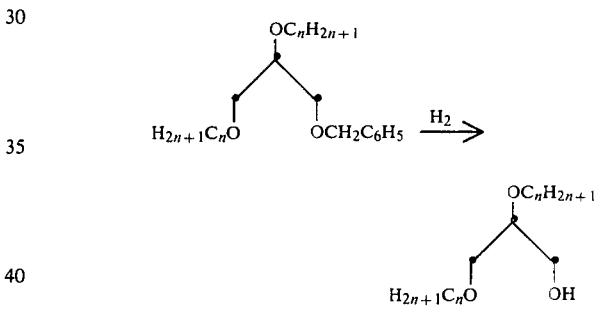

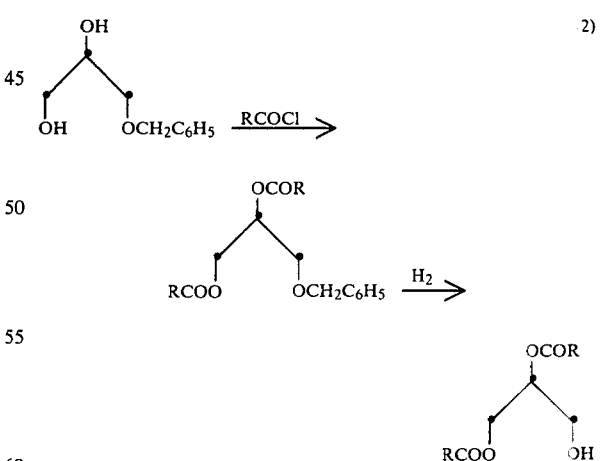

The latter esterification can be carried out in analogy with U. Heimann & F. Vögtle, Liebigs Ann.Chem. 1980, 858-862 and P. V. Ioannou, G. H. Dodd & B. T. Golding, Synthesis 1979, 939-941.

The 1,2-diaryl ethers derived from glycerol can be prepared according to the following reaction scheme:

cording to the methods described e.g. by A. J. Showler & P. A. Darley, Chem.Rev. 67, 427 (1967) and H. Hilbert & N. M. Carter, J.Am.Chem.Soc. 51, 1601 (1929).

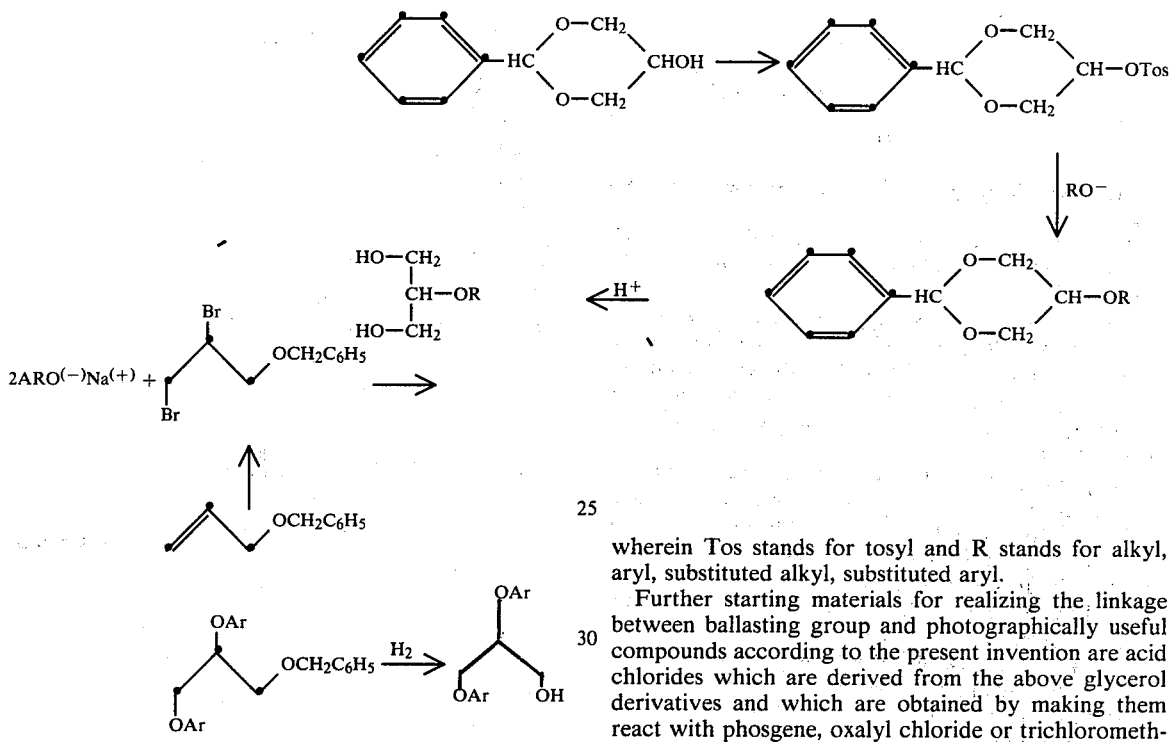

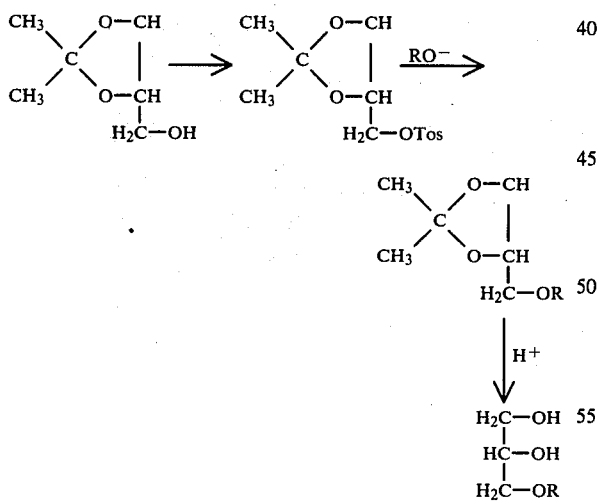

wherein Ar stands for aryl.

The α-mono-ethers derived from glycerol can be prepared according to the following reaction schemes:

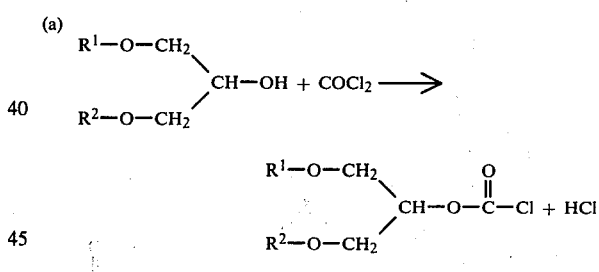

wherein:
Tos=tosyl
R=alkyl, aryl, substituted alkyl or substituted aryl.

The tosylate (-Tos) is prepared according to U. Schmidt, J. Talbiersky, F. Bartkowiak & J. Wild, Angew.Chem., 92, 201-202 (1980).

The β-mono-ethers can be prepared according to the following reaction scheme starting from 2-phenyl-5-hydroxy-1,3-dioxan which itself can be obtained acwherein Tos stands for tosyl and R stands for alkyl, aryl, substituted alkyl, substituted aryl.

Further starting materials for realizing the linkage between ballasting group and photographically useful compounds according to the present invention are acid chlorides which are derived from the above glycerol derivatives and which are obtained by making them react with phosgene, oxalyl chloride or trichloromethylchloroformate as illustrated hereinafter.

(a)
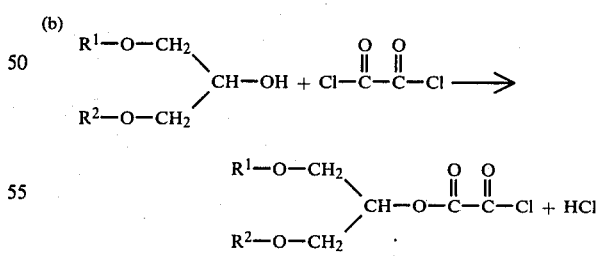

e.g. as is described in DE-OS 1,797,083.

(b)

The latter reaction can generally be performed as follows:

1.5 mol of oxalyl chloride is stirred with 75 ml of methylene chloride upon an ice-bath. To this mixture a solution of 1 mol of the alcohol in 200 ml of methylene chloride is added dropwise over a periode of about 90 minutes. The mixture is stirred for 3 h at a temperature not higher than 10° C. and is then concentrated by evaporation. The resulting oil is refined by destillation.

(c) 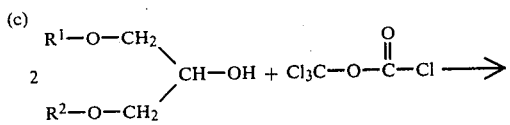

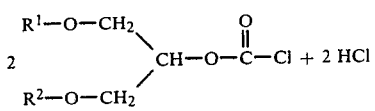

wherein $R^1$ and $R^2$ are defined as described hereinbefore.

The preparation of 1,3-di-n-hexyloxy-2-propyl-chloroformate is given hereinafter as an example of the latter synthesis.

275 g of phosgene was trapped in 1.3 l of dry toluene under acetone/dry ice cooling of the solution. Subsequently a solution of 242 g of N,N-dimethylanilin and 520 g (2 mol) of 1,3-di-n-hexyloxy-2-propanol in 2 l of dry toluene was slowly added under stirring (addition time: 2 hours).

Upon completion of the addition the reaction mixture was stirred at room temperature for another 3 h. After filtration the liquid was concentrated in a rotary evaporator and yielded 569 g of a clear liquid which was used without further purification.

The chloroformates, however, can also be generated in situ from the alcohols with trichloromethylchloroformate, as described in DE-OS No. 2,644,538.

The following preparations illustrate how the compounds according to the present invention can be obtained using the above starting materials.

was formed immediately and after 2 h of refluxing the reaction was terminated. The solution was concentrated by evaporation and the resulting oil was refined by preparative column chromatography. Yield: 18 g (23.4%). Melting point: 155° C.

Preparation 2: compound 7

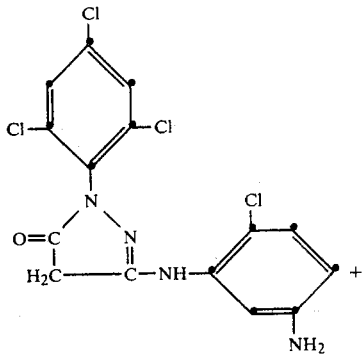

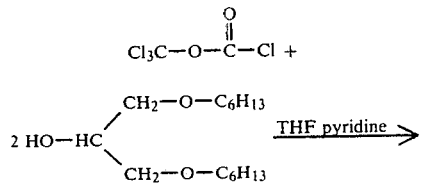

Preparation 1: compound 4

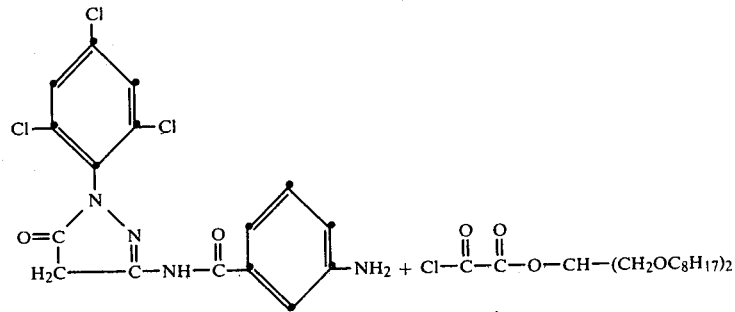

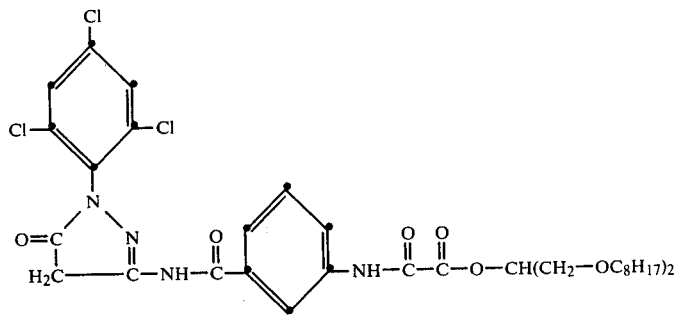

39.8 g (0.1 mol) of the 2-pyrazolin-5-one compound was refluxed in 800 ml of dioxan and 40.7 g (0.1 mol) of the acid chloride was added dropwise. A precipitate

-continued
Preparation 2: compound 7

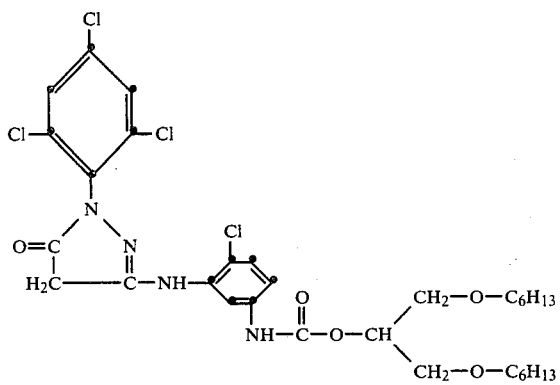

8.1 ml of trichloromethylchloroformate was dissolved in 40 ml of tetrahydrofuran (THF).

31.2 g of 1,3-dihexyloxy-2-propanol was dissolved in a mixture of 10.4 ml of pyridine and 60 ml of tetrahydrofuran (THF).

The chloroformate solution was cooled upon an ice-bath and stirred whilst the propanol solution was added dropwise to the former and the temperature was kept below 12° C. The mixture was allowed to react for another hour at room temperature and a white precipitate was formed.

46.45 g of 1-(2,4,6-trichlorophenyl)-3-(5-amino-2-chloro-anilino)-2-pyrazolin-5-one was stirred in 10 ml of pyridine and 180 ml of tetrahydrofuran (THF). This suspension was added to the reaction mixture at once whereby the temperature rose to 35° C. The mixture was further mixed at room temperature for 2 more hours. A small precipitate of impurities was filtered off. The filtrate was washed with water and was shaken out with ethyl acetate. The solution in ethyl acetate was dried upon sodium sulphate, filtered and concentrated by evaporation. The residue was dissolved in 250 ml of toluene and filtered upon silicagel whereupon the silicagel was eluted with methylene chloride.

The filtrate was concentrated by evaporation and the residue was recrystallized from a mixture of hexane:toluene (2:1). Yield: 47.5 g. Melting point: 108°–110° C.

Preparation 3: compound 8

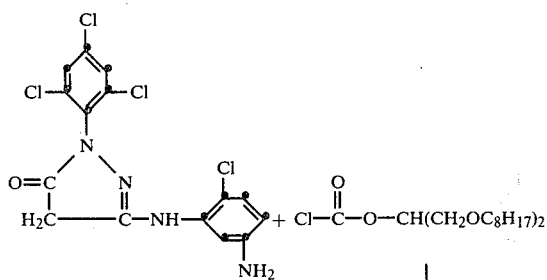

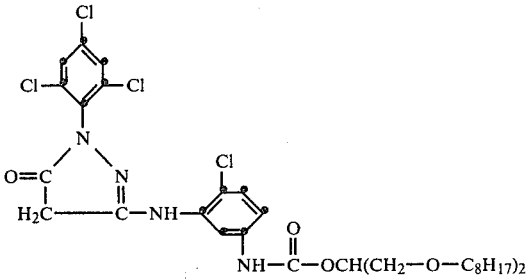

40.4 g (0.1 mol) of the 2-pyrazolin-5-one compound was stirred with 8.4 g (0.1 mol) of sodium hydrogen carbonate in 400 ml of anhydrous acetonitrile. Then 37.85 g (0.1 mol) of the chloroformate (prepared as described in DE-OS No. 1,797,083) was added dropwise to the suspension and the mixture was refluxed. After cooling, the yielded oil was extracted with ether, and the organic phase was washed until neutral and concentrated by evaporation. The refining was performed with preparative column chromatography. Yield: 17 g (22.8%). Melting point: 65°–75° C.

Preparation 4: compound 11

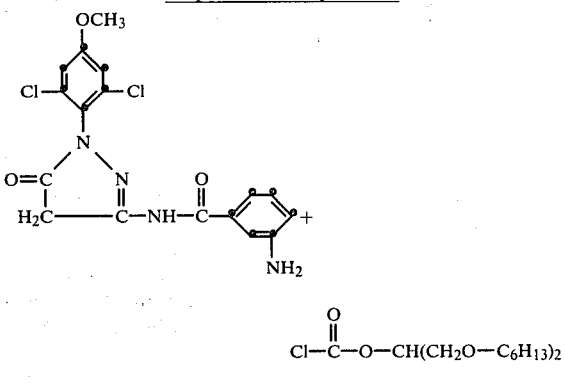

38.4 g (0.1 mol) of the 2-pyrazolin-5-one compound was stirred with 8.2 g (0.1 mol) of anhydrous sodium acetate in 320 ml of acetic acid. The temperature was kept at 40° C. and 16.2 g (0.05 mol) of the chloroformate was added dropwise. The temperature of the mixture rose and the latter was refluxed for 30 min. The mixture was then poured out into ice water, the aqueous phase was decanted and the residue was washed with acetonitrile. Yield: 20 g (29.5%). Melting point: 130° C.

Preparation 5: compound 16

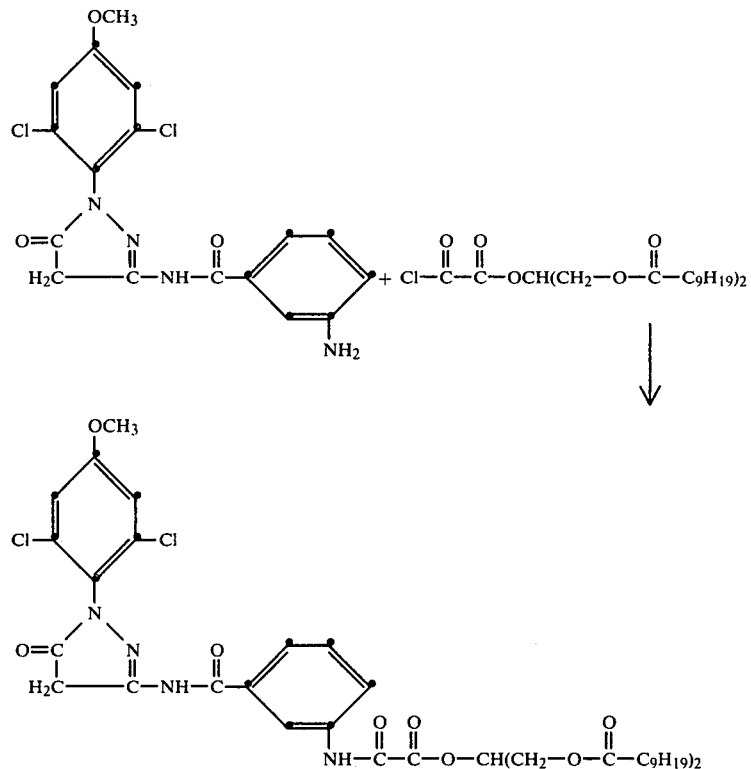

39.3 g (0.1 mol) of the 2-pyrazolin-5-one compound was refluxed in 300 ml of dioxan and 49.1 g (0.1 mol) of the chloro-oxalate was added dropwise. After a 1 h reflux the reaction was terminated, the mixture was concentrated by evaporation and was refined by preparative column chromatography. Yield: 14.2 g (16.7%) of oily product.

which 3 g of sodium hydrogen carbonate was added. Then 19.25 g (0.05 mol) of the chloro-oxalate was added whilst stirring (exothermic reaction). The mixture was refluxed for 2 h, filtered while hot and cooled to room temperature. A light-yellow product precipitated. After filtration, washing with acetonitrile and drying at 50° C., 25.2 g of the analytically pure product was obtained.

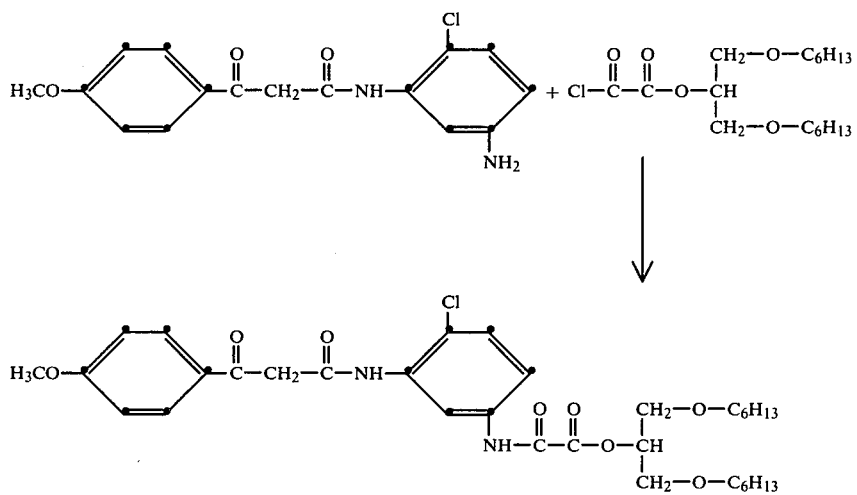

In a three-necked flask of 250 ml 15.9 g (0.05 mol) of the amine was suspended in 120 ml of acetonitrile to Melting point: 129° C.

Preparation 7: compound 31

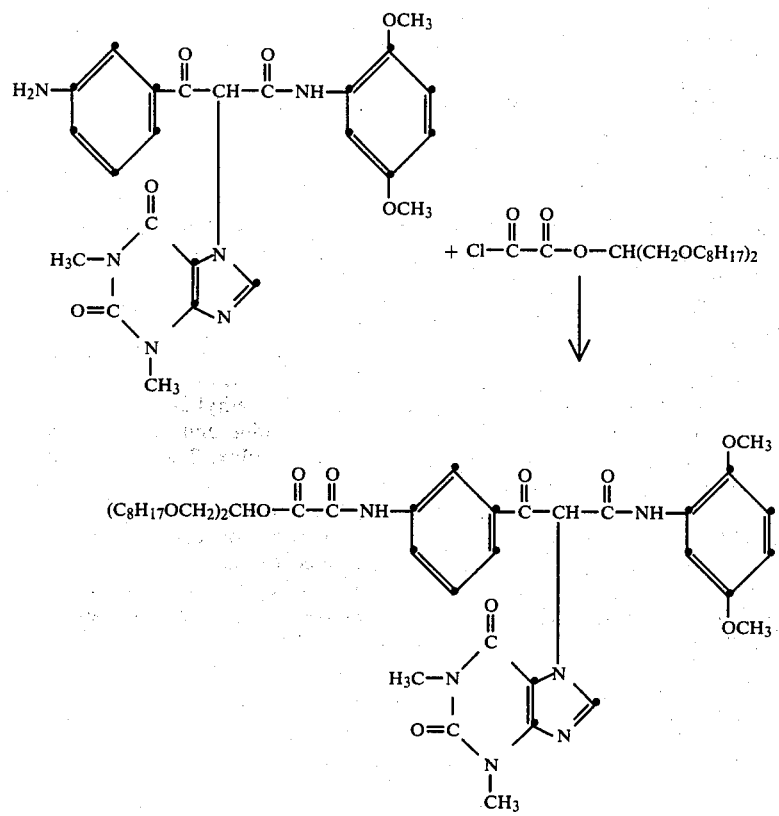

In a three-necked flask of 250 ml 24.6 g (0.05 mol) of the amine was dissolved in 120 ml of anhydrous acetonitrile to which 3 g of sodium hydrogen carbonate was added and the mixture was stirred at room temperature. Then 20.4 g (0.05 mol) of the chloro-oxalate was added dropwise whereby the temperature rose. The mixture was refluxed for 2 h and filtered whilst hot. The filtrate was concentrated by evaporation and after chromatographic refining over silica gel 26 g of the analytically pure product (resin) was yielded.

Preparation 8: compound 32

(a) 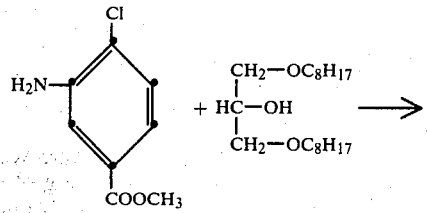

-continued
Preparation 8: compound 32

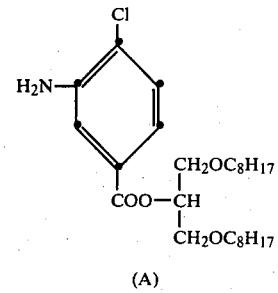

(A)

92.75 g (0.5 mol) of 3-amino-4-chloro-benzoic acid methyl ester, 158 g (0.5 mol) of glycerol-1,3-dioctyl ether and 1.25 ml of titanium tetrabutoxide were mixed with stirring and the mixture was gradually heated from 200° C. to 260° C. over about 4 h. Nitrogen was bubbled through the mixture and the formed methanol was removed over a Dufton column. Preparative column chromatography yielded 119 g of 1,3-bis-octyloxy-2-propyl-3′-amino-4′-chlorobenzoate (A), a light-brown oil.

(b) 61 g (0.13 mol) of (A) and 28.9 g (0.13 mol) of 4-methoxybenzoylacetic acid ester were boiled in 100 ml of xylene with stirring. The formed alcohol was removed via a Dufton column. After 5 h of reaction the mixture was cooled to 65° C. and methanol was added. After recrystallization from methanol some 67% of 2-(4-methoxybenzoyl)-2′-chloro-5′-(1,3-bisoctyloxy-2-propanoxy)-carbonylacetanilide (B), a white product melting at 74° C., was yielded.

(c) 45.18 g (0.07 mol) of (B) was dissolved in 140 ml of methylene chloride and 1 mol equivalent of sulphuryl chloride, dissolved in 35 ml of methylene chloride, was added over ½ h. The formed gases were collected in the drying tower of a gas absorption apparatus. Stirring at room temperature was performed for 1 h. After drying by evaporation of a light-brown oil of 2-(4-methoxybenzoyl)-2-chloro-2'-chloro-5'-(1,3-bis-octyl-2-propanoxy)-carbonylacetanilide (C) was yielded.

(d) 23.8 g (0.035 mol) of (C) was dissolved in 60 ml of acetonitrile and a solution of 6.3 g (0.035 mol) of theophylline in 8.75 ml (0.07 mol) of tetramethylguanidine and 20 ml of acetonitrile were added. After a slight exothermic reaction and when the reaction temperature was dropping, heating was performed to 40° C. for ½ h. When the reaction mixture was again at room temperature it was acidified with 8 ml of 5N hydrochloric acid. An oil was formed that solidified quickly. The latter crude product was recrystallized from ethanol and 24.45 g (85%) of 2-(4-methoxybenzoyl)-2-(7-theophyllinyl)-2-chloro-5'-(1,3-bis-octyloxy-2-propanoxy)-carbonylacetanilide, a white powder, was yielded. Melting point: 147°-148° C.

Preparation 8bis: compound 33bis (a) 144.35 g of tosyl chloride was dissolved in 220 ml of pyridine. The solution was cooled and 177.3 g of 1,3-bis-hexyloxy-2-propanol was added dropwise with stirring. After having stood overnight the mixture was poured out into a mixture of 500 ml of 5N hydrochloric acid and ice and then it was shaken out with dichloromethane. The organic phase was washed with water until free from acid, dried upon sodium sulphate, filtered and concentrated by evaporation in vacuum. Yield: 277.2 g of 1-hexyloxymethyl-2-hexyloxyethyl p-toluenesulphonate (A) (oil).

(b) 52.05 g of 3-chloro-4-nitrophenol, 45.54 g of potassium carbonate and 136.62 g of (A) were stirred in 200 ml of N-methylpyrrolidone. The mixture was heated to 135° C. and was stirred for 3 h. Then it was cooled and stirred with 1 l of water and 1 l of dichloromethane. The organic phase was washed three times with water and was then dried upon sodium sulphate and filtered. Preparative chromatography yielded 107.3 g of 1-hexyloxymethyl-2-hexyloxyethyl-3-chloro-4-nitrophenyl ether (B) (light yellow oil)

(c) 106 g of (B) and 5 ml of Raney nickel were supplemented with ethanol in order to obtain a volume of 500 ml. Reduction was performed in an autoclave under 10 MPa of hydrogen pressure at a temperature of 40° C. After shaking for 3 h the extent of hydrogen absorption attained 100%. The Raney nickel and the alcohol were removed by filtration and evaporation respectively. Yield: 98.3 g of 2-chloro-4-(1-hexyloxymethyl-2-hexyloxyethoxy)-aniline(C) (dark yellow oil).

(d) 38.55 g of (C), 24.5 g of ethyl 2-(4-methoxy-benzoyl)-acetate, 0.5 ml of butidine and 75 ml of xylene were mixed and heated to reflux. Then 60 ml of the distillate was slowly collected, whereafter reflux was continued for 3 h. After cooling, n-hexane was added and some by-product was removed by filtration. The final product was purified by chromatography. Yield: 17.8 g of 2-(4-methoxy-benzoyl)-2'-chloro-4'-(1-hexyloxymethyl-2-hexyloxyethoxy)-acetanilide (light yellow). Melting point: 34°-35° C.

Preparation 9: compound 34

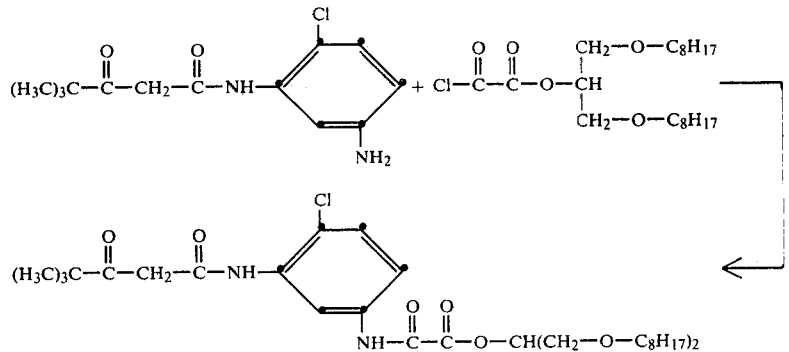

A mixture of 30.5 g (0.05 mol) of the amine, 16.8 g of sodium hydrogen carbonate and 250 ml of anhydrous acetonitrile was brought into a three-necked flask and was stirred at room temperature for 1 h. Then 41 g (0.1 mol) of the chloro-oxalate was added dropwise. After mixing for another 2 h another 6.1 g of the chloro-oxalate was added and the mixture was still stirred for 4 h. After having stood overnight the mixture was filtered and the concentrated filtrate yielded 78 g of the crude product from which 20 g of an analytically pure oil was obtained after chromatographic refining.

Preparation 10: compound 45

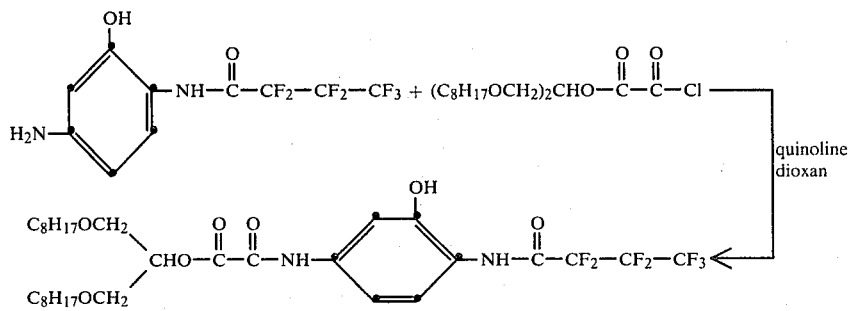

16 g (0.05 mol) of the aniline and 11.82 ml (=0.1 mol) of quinoline were dissolved in 250 ml of dioxan.

21.36 g (0.0525 mol) of the chloro-oxalate, dissolved in 40 ml of dioxan was added dropwise. The mixture was stirred for 3.5 h and left overnight. Then it was poured out into 1200 ml of ice-water and 280 ml of 2N hydrochloric acid whilst stirring. The residue was sucked off, washed acid-free and dried. Recrystallization from hexane yielded 15.3 g (44.3%) of the white product. Melting point: 85° C.

Preparation 11: compound 54

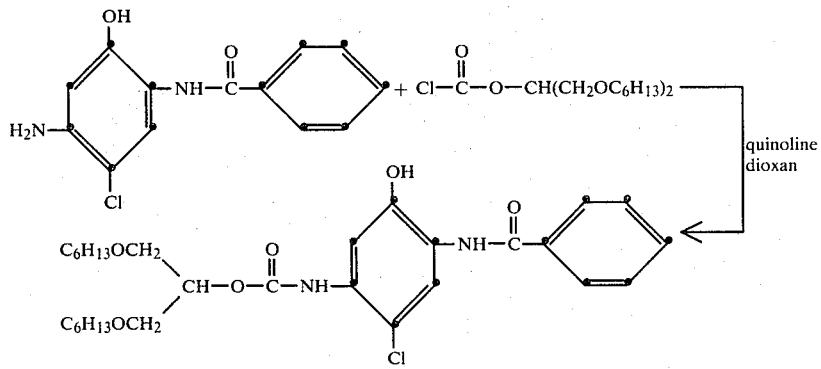

13.125 g (0.05 mol) of the aniline and 11.82 ml (0.1 mol) of quinoline were dissolved in 250 ml of dioxan.

16.93 g (0.0525 mol) of the chloroformate, dissolved in 40 ml of dioxan was added dropwise. The mixture was stirred for 2 h and left overnight. Then it was poured into 1200 ml of ice-water and 280 ml of 2N hydrochloric acid whilst stirring.

The sticky product was first sucked off, then it was dissolved in ether, washed with water, dried and concentrated by evaporation. Recrystallization was performed first from hexane, then from acetonitrile. Yield: 11 g (40%). Melting point: 93°–94° C.

Preparation 12: compound 62

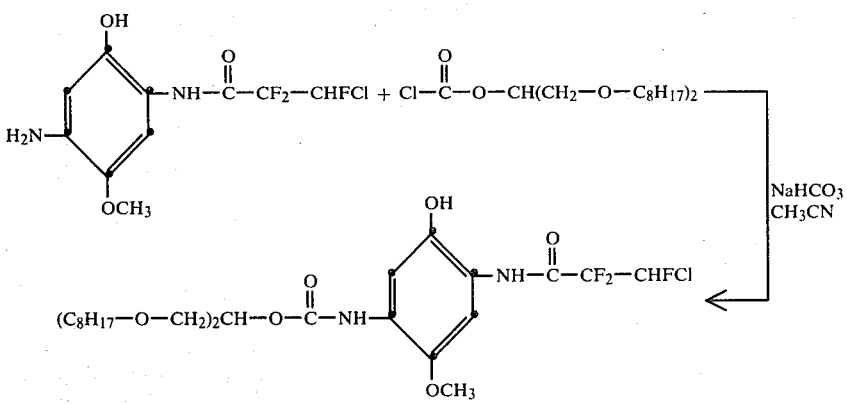

15.0 g (0.05 mol) of the aniline was stirred with 6.3 g (0.075 mol) of sodium hydrogen carbonate in 150 ml of acetonitrile at 20° C. To this suspension 20.7 g (0.055 mol) of chloroformate ester was added at once. After vigorous stirring for ½ h and adding 20 ml of 5N hydrochloric acid the suspension was diluted with 500 ml of ice-water. The precipitate was filtered and recrystallized from 250 ml of ethanol. Yield: 15.1 g (47.5%). Melting point: 93° C.

Preparation 13: compound 66

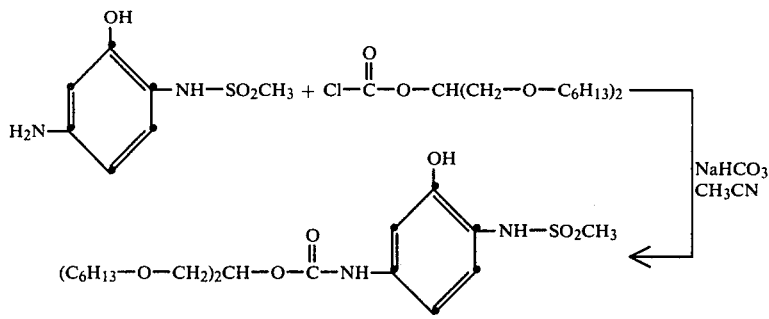

10.5 g (0.05 mol) of the amino was dissolved in 150 ml of acetonitrile at 25° C. whereupon 6.3 g (0.075 mol) of sodium hydrogen carbonate was added. To this suspension 17.5 g (0.05 mol) of the chloroformate ester was added and it was stirred vigorously for 1 h. Then 25 ml of 5N hydrochloric acid and 500 ml of ice-water were added. The precipitate was recrystallized from 250 ml of ethanol. Yield: 17.5 g (72%). Melting point: 156° C.

Preparation 14: compound 67

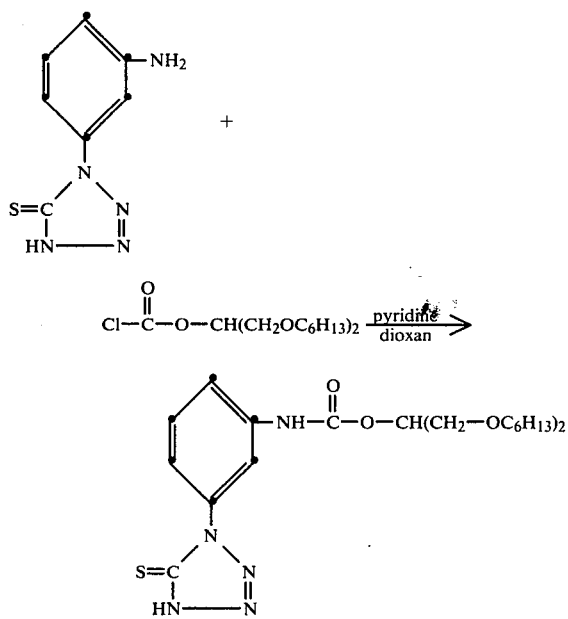

38.6 g (0.20 mol) of 1-(m-amino-phenyl)-5-mercapto-1,2,3,4-tetrazole known as a stabilizer, was stirred in 16.5 ml of pyridine and 150 ml of dioxan at 25° C. Then 65.0 g (0.21 ml) of the chloroformate ester was added dropwise to the suspension whilst the temperature was kept at 25° C. by means of an ice-bath.

After thorough stirring the suspension was diluted with 700 ml of ice-water and acidified to pH 4 with 1N hydrochloric acid. The aqueous layer was decanted and the oil phase was dissolved in 500 ml of methylene chloride.

The methylene chloride solution was washed three times with 100 ml of 1N hydrochloric acid until it was free from amines and then it was dried upon magnesium sulphate.

After concentration by evaporation and chromatographic refining 16.0 g of the amorphous compound was obtained. Melting point: 50° C. (decomposition).

The present invention further provides photographic light-sensitive materials including materials for diffusion transfer processes containing at least one light-sensitive silver halide emulsion layer and comprising in one or more hydrophilic colloid layers at least one photographically useful compound ballasted according to the present invention.

The compounds of the invention are preferably incorporated into hydrophilic colloid media from solutions in high-boiling sparingly water-miscible solvents such as di-n-butyl phthalate and tricresyl phosphate or in low-boiling sparingly water-miscible solvents such as ethyl acetate, methylene chloride, or chloroform, or mixtures thereof since they have a high solubility therein and very fine dispersions in hydrophilic colloid compositions of the compounds of the invention can be obtained by means of these solvents. For this purpose these solutions are dispersed in extremely fine droplets, preferably in the presence of a wetting or dispersing agent into the hydrophilic colloid medium, the low-boiling sparingly water-miscible solvent then being removed by evaporation.

Of course, the compounds of the invention can also be incorporated into the hydrophilic colloid composition in other ways. For instance, when the compound can be liquefied by slight heating (when it has a low melting point) or when it is liquid at room temperature the liquid can be dispersed as such in the hydrophilic colloid composition.

The hydrophilic colloid composition into which the compounds of the invention are dispersed need not necessarily be the coating composition itself of the hydrophilic colloid layer such as a silver halide emulsion layer into which the compounds are intended to be present. Especially in the case of photographic emulsion components that are intended to be incorporated into light-sensitive silver halide emulsions, it may be advantageous to first disperse the components into non-light-sensitive hydrophilic colloid compositions or into water, whereupon the dispersions in their turn are admixed with the colloid coating composition such as a silver halide emulsion, from which the hydrophilic colloid layer will be coated.

For more details about suitable dispersing techniques that may be employed for incorporating the compounds of the invention into a hydrophilic colloid layer of a photographic material reference can be made to e.g. U.S. Pat. Nos. 2,269,158, 2,284,887, 2,304,939, 2,304,940 and 2,322,027; GB Pat. No. 791,219; FR Pat. No. 1,555,663; DE Pat. No. 1,127,714 and to BE Pat. No. 747,589.

The photographically useful compounds ballasted according to the present invention are particularly suitable for being dispersed into water, even in high concentrations, which obviously is particularly important for manufacturing purposes.

The application of such ballasting groups makes it possible to prepare easily and systematically no gelatin containing highly concentrated aqueous dispersions substantially independent of the structure of the remainder of the molecule according to the method set forth in U.S. Pat. No. 3,658,546.

The following example illustrates the particular suitability of the compounds according to the invention for being dispersed into water as compared with structurally analogous compounds ballasted in the conventional way.

EXAMPLE 1

(a) dispersing procedure:

1 g of a ballasted colour coupler as defined in the tables hereinafter was dissolved in 5 ml of ethyl acetate at room temperature. The solution was dispersed at 65° C. by means of a homogenizer in 5 ml of distilled water in the presence of 1 ml of a 10% aqueous solution of a wetting agent having the formula:

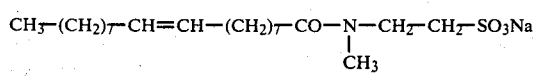

The ethyl acetate was substantially removed by evaporation under reduced pressure (27–53 kPa) at 55° C. whereupon distilled water was added up to a total volume of 6.7 ml.

An aqueous dispersion of 15% of colour coupler was yielded, suitable for admixture with a conventional gelatin silver halide emulsion ready for coating.

The following tables XVII and XVIII illustrate the possibility to obtain stable aqueous solutions with magenta and cyan forming colour couplers respectively ballasted according to the present invention.

TABLE XVII

| Compound | Dispersable | Stability after 24 h at 40° C. | Stability after 1 week at 40° C. |
|---|---|---|---|
| Reference I | no | — | — |
| Reference II | yes | crystallization | crystallization |
| 17 | yes | good | good |
| 4 | yes | good | good |
| 14 | yes | good | good |

The reference compounds I and II correspond to the following formulae:

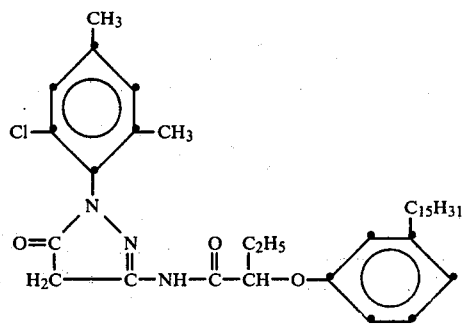

Reference I

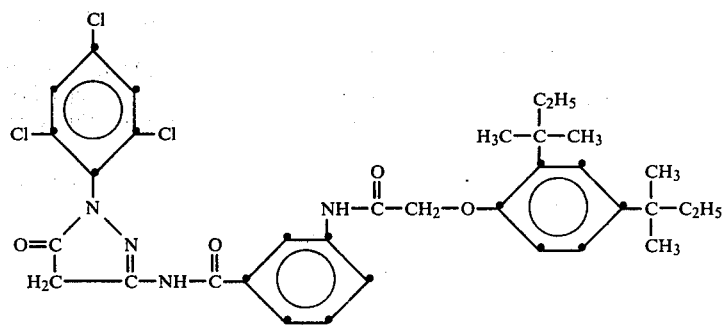

Reference II

TABLE XVIII

| Compound | Dispersable | Stability after 24 h at 40° C. | Stability after 1 week at 40° C. |
|---|---|---|---|
| Reference III | yes | crystallization | crystallization |
| 44 | yes | good | good |
| 40 | yes | good | good |

The reference compound III corresponds to the formula:

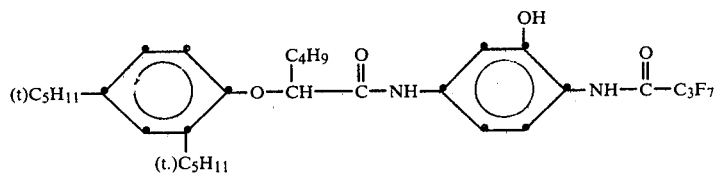

Reference III

Furthermore, we have found that photographically useful compounds ballasted according to the present invention have a relatively low melting point, their melting point generally being substantially lower than that of corresponding compounds provided with a different type of ballasting group as can be seen from the following tables XIX, XX and XXI. The lower melting point favours the stability of the dispersions upon storage due to a reduced tendency to crystallization.

TABLE XX-continued

| Compound | Melting point (°C.) |
|---|---|
| 4 | 155 |
| 5 | 110 |
| 6 | 100 |

Reference compound V corresponds to the following formula:

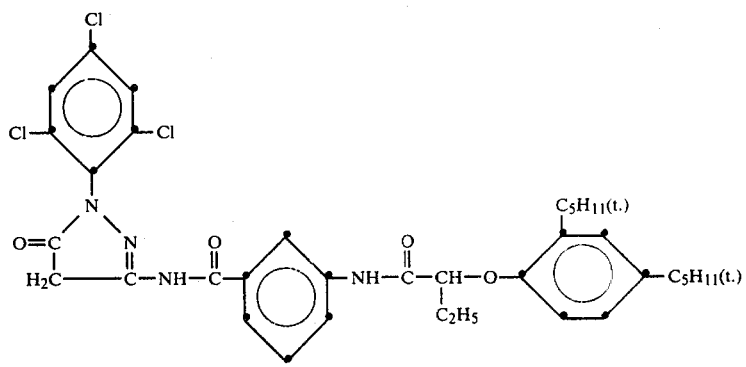

Reference V

TABLE XIX

| Compound | Melting point (°C.) |
|---|---|
| Reference IV | 167 |
| 11 | 130 |
| 12 | 130-138 |
| 13 | 66-100 |
| 14 | 100 |

TABLE XXI

| Compounds | Melting point (°C.) |
|---|---|
| Reference III | 159 |
| 44 | <50 |
| 45 | 85 |
| 46 | 89 |

The reference compound IV has the following formula:

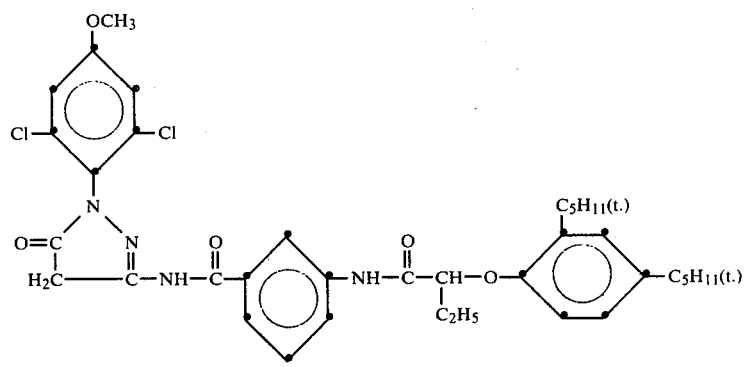

Reference IV

TABLE XX

| Compound | Melting point (°C.) |
|---|---|
| Reference V | 160 |
| 1 | 156 |
| 2 | 70-130 |
| 3 | 128 |

It has further been found that the structural nature of ballasting groups according to the invention has a favourable influence upon the micro-structure of the dye aggregates generated upon colour development from couplers containing a ballasting group according to the invention.

In this respect we can for instance refer to the following example illustrating how colour couplers ballasted according to the present invention produce upon colour development dyes having less side-absorption in the non-desirable regions of the spectrum than conventionally ballasted colour couplers.

EXAMPLE 2

Ballasted colour couplers as listed in the tables hereinafter were dispersed in hydrophilic colloid media according to the following technique.

83 ml of 5% gelatin was mixed with 5 to 10% of an emulgator based on the weight of gelatin. The mixture was dispersed at 40° C. Within 30 s a solution of 6 mmol of the colour couplers and an equal weight of dibutyl phthalate in 18–36 ml of ethyl acetate were added with stirring. Then the acetic ester was removed from the mixture by bringing the latter into a rotating thin-layer evaporator at 60° C. and about 5 kPa.

110 g of a silver bromo-iodide emulsion (with 2.3% iodide) having a gelatin content of 85.8 g per kg and a silver halide content corresponding to 50 g of silver nitrate per kg was mixed in molten state with 154.4 g of 7.5% aqueous gelatin, whereupon water was added in an amount of 100 ml for a yellow- or a cyan-forming coupler or of 200 ml for a magenta-forming coupler.

The mixture was left at 40° C. for 1 h whereupon 6 mmol of the colour coupler dispersion was added with stirring together with the usual additives such as hardeners, wetting agents and stabilizers. Finally water was added up to a total weight of 575 g (for a yellow- or a cyan-forming coupler) or 720 g (for a magenta-forming coupler).

The solution was then coated onto a cellulose acetate base in an amount of 150 g per sq.m for a yellow-forming coupler or of 125 g per sq.m for a magenta or a cyan-forming coupler.

After exposure to light of the appropriate wavelength through a grey wedge, the photographic materials formed were developed at 24° C. for 10 min in a colour developing bath of the following composition:
2 g of sodium hexametaphosphate
4 g of anhydrous sodium sulphite
17 g of anhydrous sodium carbonate
2 g of potassium bromide
3 g of 2-amino-5-diethylaminotoluene hydrochloride
water up to 1 l.

Subsequently the developed materials were treated at 24° C. for 5 min in the following acid fixing bath:
800 ml of water
200 g of anhydrous sodium thiosulphate (or 300 g of sodium thiosulphate pentahydrate)
12 g of potassium bisulphite
12 ml of glacial acetic acid
20 g of borax
15 g of potassium alum water up to 1 l.

The materials were then rinsed with water (21° C.) for 10 min and subsequently subjected to a bleaching bath (21° C., 7 min) of the following composition:
20 g of potassium bromide
5 g of potassium dichromate
40 g of potassium alum
water up to 1 l.

After bleaching the materials were rinsed at 15° C. for 5 min and fixed again in the fixing bath mentioned above (at 24° C. for 5 min). After another rinsing at 15° C. for 10 min the materials were stabilized by a 20 s immersion in a stabilizing bath with the following composition:
1.8 ml of 5% saponin
12.8 ml of 40% formaldehyde
water up to 1 l.

Strips of so exposed and processed photographic materials were sensitometrically evaluated upon a colour densitometer e.g. a Joyce-Gevaert colour densitometer as described in British Cinematography, Vol. 38, no. 1, Jan. 1961, p. 4–7—A Recording Colour Densitometer by A. Thiels. The latter apparatus was provided with interference filters which have a very narrow spectral field of measurement (blue 436 nm, green 546 nm, red 644 nm). The density curves were registered at these three wavelengths. Measurement of side-densities was performed at the colour density 1.00 above colour fog of the main density. The values for the colour fog were subtracted from the measured side-densities and from the resulting density values the percentage of side-absorption was calculated.

The calculated values are listed in the following tables XXII, XXIII and XXIV.

TABLE XXII

| Compound | λ max (nm) | Side-absorptions (%) in blue region | in red region |
|---|---|---|---|
| Reference V | 558 | 20 | 21 |
| 1 | 556 | 18 | 15 |
| 2 | 556 | 19 | 12 |
| 4 | 553 | 17 | 12 |
| 5 | 551 | 19 | 12 |
| 11 | 549 | 20 | 14 |
| 14 | 545 | 17 | 10 |
| 15 | 545 | 18 | 10 |
| 16 | 545 | 20 | 10 |

One can readily see from Table XXII that the use of compounds ballasted according to the invention involves substantially less side-absorptions than the reference.

TABLE XXIII

| Compound | λ max (nm) | Side-absorptions (%) in blue region | in red region |
|---|---|---|---|
| Reference VI | 549 | 12 | 9 |
| 8 | 546 | 11 | 6 |
| 17 | 551 | 10 | 6 |

Reference compound VI corresponds to the following formula:

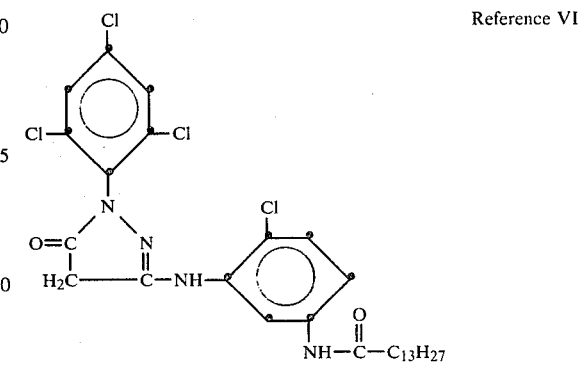

Reference VI

The use of compounds ballasted according to the present invention involves less side-adsorptions than the reference 3-anilinopyrazolone colour coupler provided with a different type of ballast group.

TABLE XXIV

| Compound | λ max (nm) | Side-absorptions (%) in blue region | in green region |
|---|---|---|---|
| Reference VII | 673 | 11 | 15 |
| Reference III | 678 | 10 | 15 |
| 36 | 652 | 5 | 14 |
| 37 | 651 | 5 | 14 |
| 38 | 655 | 4 | 13 |
| 41 | 662 | 7 | 15 |

The reference compound VII corresponds to the following formula:

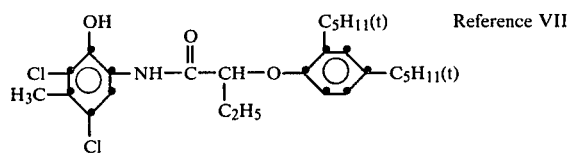

The use of cyan-forming colour couplers ballasted according to the present invention involves less side-absorptions than conventionally ballasted cyan-forming colour couplers.

The conformation of colour couplers is affected by the nature of the ballasting groups incorporated into their molecules. As a result their reactivity can be manipulated to some extent by variation of the type of the ballasting group.

In this respect the following example illustrates the increased reactivity of couplers ballasted according to the invention relative to couplers with conventional ballasting groups.

EXAMPLE 3

Ballasted colour couplers as listed in the table hereinafter were introduced in photographic materials and processed as described in example 2.

The sensitometric results are listed in table XXV.

TABLE XXV

| Compound | Sensitivity | Gamma | Maximum density |
|---|---|---|---|
| Reference III | Reference | 1.42 | 3.00 |
| 64 | + 1°DIN | 2.11 | 3.58 |
| 45 | + 1.3°DIN | 2.09 | 3.86 |

Although the hydrophilic colloid media in which the compounds according to the invention are incorporated usually comprise gelatin as hydrophilic colloid, other water-soluble colloidal materials or mixtures of them can be used too e.g. colloidal albumin, zein, casein, a cellulose derivative such as carboxymethylcellulose, or a synthetic hydrophilic colloid such as polyvinyl alcohol, and poly-N-vinylpyrrolidone.

The compounds of the invention may be used in photographic materials comprising various kinds of photographic emulsion layers. Various silver salts may be used as the sensitive salt such as silver bromide, silver iodide, silver chloride and mixed silver halides such as silver chlorobromide, silver bromoiodide and silver chlorobromoiodide.

The light-sensitive silver halide emulsions may be chemically as well as optically sensitized. They may be chemically sensitized by effecting the ripening in the presence of small amounts of sulphur-containing compounds such as allyl thiocyanate, allylthiourea, and sodium thiosulphate. The emulsions may also be sensitized by means of reductors for instance tin compounds as described in FR Pat. No. 1,146,955 and in BE Pat. No. 568,687, imino-amino methane sulphinic acid compounds as described in GB Pat. No. 789,823 and small amounts of noble metal compounds such as gold, platinum, palladium, iridium, ruthenium and rhodium compounds. They may be optically sensitized by means of cyanine and merocyanine dyes.

The said emulsions may also comprise compounds which sensitize the emulsions by development acceleration for example compounds of the polyoxyalkylene type such as alkylene oxide condensation products as described among others in U.S. Pat. Nos. 2,531,832, 2,533,990, 3,210,191 and 3,158,484, in GB Pat. Nos. 920,637 and 991,608 and in BE Pat. No. 648,710 and onium derivatives of amino-N-oxides as described in GB Pat. No. 1,121,696.

Further, the emulsions may comprise stabilizers, e.g. heterocyclic nitrogen-containing thioxo-compounds such as benzothiazoline-2-thione and 1-phenyl-2-tetrazoline-5-thione and compounds of the hydroxytriazolopyrimidine type. They can also be stabilized with mercury compounds such as the mercury compounds described in BE Pat. No. 524,121, 677,337 and 707,386 and in U.S. Pat. No. 3,179,520.

The light-sensitive emulsions may also comprise all other kinds of ingredients such as plasticizers, hardening agents, and wetting agents.

The emulsions can be coated on a wide variety of photographic emulsion supports. Typical supports include cellulose ester film, polyvinylacetal film, polystyrene film, polyethylene terephthalate film and related films of resinous materials, as well as paper and glass.

We claim:

1. A photographic element comprising one or more light-sensitive silver halide emulsion layers and in one or more hydrophilic colloid layers at least one compound comprising one or two photographically useful groups and a ballasting group that is structurally derived from glycerol wherein one or two —OH group(s) is/are converted to —OR group(s) and the remaining —OH group(s) is/are converted to —X—L— molecular parts linking the said ballasting group to the said photographically useful group or groups and wherein:

R is an organic group with the proviso that when two of said —OR group are present, the said —R groups together contain not less than 5 hydrocarbon C-atoms;

X is —O—, —S— or —NY—, where Y is H or a $C_1$-$C_5$ alkyl group, and

L is a chemical bond or a group linking X to the said photographically useful group or groups.

2. A photographic element according to claim 1, characterized in that the said ballasting group corresponds to one of the following general formulae:

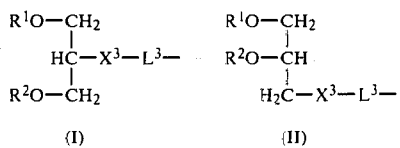

-continued $$\begin{array}{cc} \text{H}_2\text{C}-\text{X}^1-\text{L}^1- & \text{H}_2\text{C}-\text{X}^1-\text{L}^1- \\ | & | \\ \text{R}^3\text{O}-\text{CH} & \text{HC}-\text{X}^2-\text{L}^2- \\ | & | \\ \text{H}_2\text{C}-\text{X}^2-\text{L}^2- & \text{R}^3\text{O}-\text{CH}_2 \\ \text{(III)} & \text{(IV)} \end{array}$$

wherein:
- each of $X^1$, $X^2$, $X^3$ (the same or different) represents $-O-$, $-S-$ or $-NY-$, wherein Y stands for hydrogen or a $C_1-C_5$ alkyl group;
- each of $L^1$, $L^2$, $L^3$ (the same or different) stands for a chemical bond or a group linking $X^1$, $X^2$ or $X^3$ to a photographically useful group, and
- each of $R^1$, $R^2$, $R^3$ (the same or different) stands for alkyl, aryl, acyl and/or substituted alkyl, aryl, acyl (e.g. alkylcarbonyl, acyl and/or substituted alkyl, aryl, acyl (e.g. alkylcarbonyl, alkylsulphonyl, alkylaminocarbonyl, alkoxycarbonyl, dialkylaminocarbonyl . . . ) with the proviso that $R^1+R^2$ comprise together at least 5 hydrocarbon C-atoms.

3. A photographic element according to claim 2, wherein each of the linkages $L^1$, $L^2$ or $L^3$ is formed by at least one bivalent mono- or polyatomic group.

4. A photographic element according to claim 3, wherein each of $L^1$, $L^2$ or $L^3$ stands for a group selected from $-CO-$, $-SO_2-$, $-COO-$, $-CO-NY'-$, $-CO-CO-NY'-$, $-SO_2-NY'-$, wherein Y' is hydrogen or a $C_1-C_5$ alkyl group, or from alkylene, arylene, substituted alkylene or substituted arylene.

5. A photographic element according to claim 1, wherein the photographically useful group is a colour coupler.

* * * * *